US007767876B2

(12) United States Patent
Davis et al.

(10) Patent No.: US 7,767,876 B2
(45) Date of Patent: Aug. 3, 2010

(54) DISPOSABLE ABSORBENT ARTICLE HAVING A VISIBLY HIGHLIGHTED WETNESS SENSATION MEMBER

(75) Inventors: Mary Elizabeth Davis, Madeira, OH (US); Donald Carroll Roe, West Chester Township, OH (US); Patrick Jay Allen, Montgomery, OH (US); Edward Paul Carlin, Deerfield Township, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 311 days.

(21) Appl. No.: 10/697,225

(22) Filed: Oct. 30, 2003

(65) Prior Publication Data

US 2005/0096612 A1 May 5, 2005

(51) Int. Cl.
*A61F 13/15* (2006.01)
(52) U.S. Cl. .............. 604/361; 604/367; 604/368; 604/369; 604/378; 604/381; 604/384; 604/385.01; 604/385.25; 604/385.27; 604/385.28; 206/458; 600/362
(58) Field of Classification Search .............. 604/361, 604/367, 368–369, 378, 381, 384, 385.01, 604/385.23–385.28; 206/458; 600/362
See application file for complete search history.

(56) References Cited

U.S. PATENT DOCUMENTS

| | | | |
|---|---|---|---|
| 2,043,325 A | | 6/1936 | Jackson, Jr. |
| 3,794,024 A | | 2/1974 | Kokx et al. |
| 3,927,673 A | | 12/1975 | Taylor |
| 3,934,588 A | | 1/1976 | Mesek et al. |
| 4,022,211 A | * | 5/1977 | Timmons et al. ............ 604/361 |
| 4,106,001 A | | 8/1978 | Mahoney |
| 4,657,538 A | | 4/1987 | Becker et al. |
| 4,738,674 A | * | 4/1988 | Todd et al. ............ 604/361 |

(Continued)

FOREIGN PATENT DOCUMENTS

EP 0 119 919 9/1984

(Continued)

OTHER PUBLICATIONS

U.S. Appl. No. 11/281,791, filed Nov. 17, 2005. All Office Actions and Responses beginning May 28, 2008.

*Primary Examiner*—Tatyana Zalukaeva
*Assistant Examiner*—Ginger T Chapman
(74) *Attorney, Agent, or Firm*—Amy M. Foust; Matthew P. Fitzpatrick

(57) ABSTRACT

A disposable absorbent article including a wetness sensation member and visible highlighting indicating the presence of the wetness sensation member to facilitate an opportunity for the toilet training of the wearer. The wetness sensation member includes a permeable layer and a flow control layer. Urine deposited on the wetness sensation member can penetrate through the permeable body-facing layer in a z direction away from the wearer to the flow control layer. The flow control layer retards the passage of the urine through the wetness sensation member in the z direction while supporting the movement of the urine in an x-y plane to increase the wetted area contacting the wearer's skin and thereby enhance the wearer's awareness that urination has occurred. The visible highlighting is visible when viewing a body-facing surface of the article and may be associatively correlated with an externally visible marking and/or with the concept of toilet training.

6 Claims, 9 Drawing Sheets

U.S. PATENT DOCUMENTS

| | | | | |
|---|---|---|---|---|
| 4,778,459 A | | 10/1988 | Fuisz | |
| 4,834,733 A | * | 5/1989 | Huntoon et al. | 604/361 |
| 5,266,592 A | | 11/1993 | Grub et al. | |
| 5,277,180 A | | 1/1994 | Angelillo et al. | |
| 5,342,343 A | | 8/1994 | Kitaoka et al. | |
| 5,468,236 A | * | 11/1995 | Everhart et al. | 604/361 |
| 5,522,809 A | * | 6/1996 | Larsonneur | 604/361 |
| 5,649,914 A | | 7/1997 | Glaug et al. | |
| 5,658,268 A | | 8/1997 | Johns et al. | |
| 5,681,298 A | | 10/1997 | Brunner et al. | |
| 5,702,376 A | | 12/1997 | Glaug et al. | |
| 5,728,125 A | | 3/1998 | Salinas | |
| 5,797,892 A | * | 8/1998 | Glaug et al. | 604/361 |
| 5,823,953 A | * | 10/1998 | Roskin et al. | 600/367 |
| 5,846,230 A | | 12/1998 | Osborn, III et al. | |
| 5,885,264 A | * | 3/1999 | Matsushita | 604/361 |
| 5,891,124 A | | 4/1999 | Nomura et al. | |
| 5,910,447 A | * | 6/1999 | Lawrence et al. | 436/111 |
| 5,947,947 A | | 9/1999 | Tanzer et al. | |
| 6,075,178 A | * | 6/2000 | La Wilhelm et al. | 604/361 |
| 6,114,597 A | | 9/2000 | Romare | |
| 6,126,597 A | * | 10/2000 | Smith et al. | 600/362 |
| 6,146,367 A | * | 11/2000 | Otsubo et al. | 604/385.01 |
| 6,169,225 B1 | * | 1/2001 | Otsubo | 604/361 |
| 6,200,668 B1 | | 3/2001 | Kronzer | |
| 6,203,496 B1 | * | 3/2001 | Gael et al. | 600/362 |
| 6,229,063 B1 | | 5/2001 | Shimoe et al. | |
| 6,297,424 B1 | | 10/2001 | Olson et al. | |
| 6,307,119 B1 | * | 10/2001 | Cammarota et al. | 604/361 |
| 6,320,096 B1 | * | 11/2001 | Inoue et al. | 604/378 |
| 6,426,227 B1 | * | 7/2002 | Kritzman et al. | 436/43 |
| 6,515,194 B2 | | 2/2003 | Neading et al. | |
| 6,617,488 B1 | * | 9/2003 | Springer et al. | 604/361 |
| 6,627,394 B2 | * | 9/2003 | Kritzman et al. | 435/4 |
| 6,627,786 B2 | * | 9/2003 | Roe et al. | 604/361 |
| 6,630,096 B2 | | 10/2003 | Inoue et al. | |
| 6,642,427 B2 | * | 11/2003 | Roe et al. | 604/361 |
| 6,657,099 B1 | * | 12/2003 | Underhill et al. | 604/361 |
| 6,710,221 B1 | | 3/2004 | Pierce et al. | |
| 6,793,649 B1 | | 9/2004 | Fujioka et al. | |
| 7,033,934 B2 | | 4/2006 | Iijima et al. | |
| 2001/0049513 A1 | * | 12/2001 | Neading et al. | 604/361 |
| 2001/0053898 A1 | * | 12/2001 | Olson et al. | 604/361 |
| 2002/0143316 A1 | | 10/2002 | Sherrod et al. | |
| 2002/0169427 A1 | * | 11/2002 | Roe et al. | 604/361 |
| 2003/0014025 A1 | * | 1/2003 | Allen et al. | 604/361 |
| 2003/0100872 A1 | * | 5/2003 | Roe et al. | 604/361 |
| 2003/0114807 A1 | | 6/2003 | Underhill et al. | |
| 2003/0114821 A1 | * | 6/2003 | Underhill et al. | 604/383 |
| 2003/0199845 A1 | | 10/2003 | Roe et al. | |
| 2004/0199133 A1 | | 10/2004 | Underhill et al. | |
| 2004/0220540 A1 | | 11/2004 | Underhill et al. | |
| 2005/0096612 A1 | | 5/2005 | Davis et al. | |
| 2005/0222546 A1 | * | 10/2005 | Vargo et al. | 604/361 |
| 2006/0224132 A1 | * | 10/2006 | Roe et al. | 604/361 |
| 2006/0264858 A1 | * | 11/2006 | Roe et al. | 604/361 |
| 2007/0032772 A1 | * | 2/2007 | Ehrnsperger et al. | 604/385.28 |
| 2007/0191797 A1 | * | 8/2007 | Roe et al. | 604/361 |
| 2007/0233026 A1 | * | 10/2007 | Roe et al. | 604/361 |
| 2007/0287971 A1 | * | 12/2007 | Roe et al. | 604/361 |
| 2008/0065034 A1 | * | 3/2008 | Vargo et al. | 604/361 |
| 2008/0071239 A1 | * | 3/2008 | Nandrea et al. | 604/361 |
| 2008/0195072 A1 | * | 8/2008 | Warner | 604/385.01 |

FOREIGN PATENT DOCUMENTS

| | | | |
|---|---|---|---|
| EP | 0 861 645 A2 | | 9/1998 |
| EP | 0 904 758 A2 | | 3/1999 |
| EP | 0 919 213 A2 | | 6/1999 |
| GB | 2 244 201 A | | 11/1991 |
| GB | 2244201 A | * | 11/1991 |
| JP | 59-190230 U | | 12/1984 |
| WO | WO 91/19471 | * | 12/1991 |
| WO | WO 96/12459 A2 | | 5/1996 |
| WO | WO 96/19168 | | 8/1996 |
| WO | WO 00/76442 | | 12/2000 |
| WO | WO 03/045298 | | 6/2003 |

* cited by examiner

DISPOSABLE ABSORBENT ARTICLE HAVING A VISIBLY HIGHLIGHTED WETNESS SENSATION MEMBER

FIELD OF THE INVENTION

This invention is directed to hygienic disposable absorbent articles, such as diapers, training pants, incontinence garments, and the like. This invention is particularly related to disposable absorbent articles that are specially adapted for use in urinary toilet training.

BACKGROUND OF THE INVENTION

Absorbent articles are well known in the art. These articles typically have an absorbent core held or positioned in proximity to the body of a wearer during use in order to capture and absorb bodily exudates discharged from the wearer. Typical absorbent articles include a topsheet facing the wearer, which permits fluid exudates to pass through, and a backsheet, which prevents the exudates from escaping from the absorbent article.

Disposable absorbent articles such as diapers are designed to absorb and contain bodily waste in order to prevent soiling of the body and clothing of the wearer. Disposable diapers typically comprise a single design available in different sizes to fit a variety of wearers ranging from newborns to toddlers undergoing toilet training. The design of the diaper typically affects performance, such as the ability to absorb and contain bodily waste. The fit of the diaper on the wearer's body is typically affected by, for example, the size of the diaper waist opening, the size of the openings around the thighs, and the length or "pitch" of the diaper.

The toilet training stage may be referred to as the "point of exit" from the diaper product category because toddlers who have successfully completed toilet training typically no longer wear diapers. The age at which children are toilet trained in "developed" countries has increased steadily over the past several decades and is now in the range of about 24-48 months. One reason for which toilet training has become delayed is that significant technical improvements have been made in diaper dryness and comfort. For example, when wearing a typical modern diaper, the child may have dry skin even after one or more occurrences of urination. As a result, the child may feel little or no discomfort and often may not even be aware that he or she has urinated.

Many parents have the child wear cotton training pants or cotton underwear during urinary toilet training so the child feels discomfort following urination in his or her "pants". It is believed that such discomfort assists with learning or provides motivation to learn to voluntarily retain urine. Cotton training pants leave the skin wet and, due to their high breathability, promote evaporative cooling of the skin, further enhancing discomfort. The current tradeoff in this approach, however, is that cotton training pants have poor urine containment, leading to wet clothing and often times, wet surroundings, e.g., carpeting, furniture, etc. Clearly, there is a need to provide a training signal to the child undergoing urinary toilet training while preventing urine leakage and unnecessary changes of clothing.

Thus, it would be desirable to provide an article that can facilitate urinary toilet training by enhancing a wearer's awareness that urination has occurred while at the same time providing the protection of an absorbent article to prevent soiling of the wearer's clothing and surroundings. Particularly, it would be desirable to provide such an article in a form that also provides an effective signal of urination by ensuring that the wearer feels an uncomfortable wetness sensation resulting from urination. In addition, it would be desirable to visibly highlight the presence in the article of the feature that provides this wetness sensation to facilitate an opportunity for urinary toilet training.

SUMMARY OF THE INVENTION

A disposable absorbent article is provided with a wetness sensation member that enhances the wearer's awareness that a discharge of bodily exudates, such as urine, has occurred. The wetness sensation member comprises a permeable layer and a flow control layer disposed in a face-to-face arrangement with the permeable layer. Once the wearer urinates, wetting an area of the wetness sensation member, the urine penetrates through the thickness of the permeable layer in the z-direction to the flow control layer, which retards the passage of the urine through the wetness sensation member in the z direction and supports the movement of the urine in an x-y plane. This enables the urine to wet a large area of the wetness sensation member before being absorbed into the absorbent core. The wetness sensation member is held in contact with the wearer's skin during use and thereby enhances the wearer's awareness that urination has occurred. The presence of the wetness sensation member in the article is visibly highlighted to facilitate an opportunity for toilet training.

BRIEF DESCRIPTION OF THE DRAWINGS

While the specification concludes with claims particularly pointing out and distinctly claiming the subject matter which is regarded as forming the present invention, it is believed that the invention will be better understood from the following description which is taken in conjunction with the accompanying drawings in which like designations are used to designate like elements, and in which:

FIG. 5b is a cross sectional view of the diaper illustrated in FIG. 5a.

FIG. 6b is a cross sectional view of the diaper illustrated in FIG. 6a.

FIG. 7b is a cross sectional view of the diaper illustrated in FIG. 7a.

FIG. 8b is a cross sectional view of the diaper illustrated in FIG. 8a.

FIG. 9b is a cross sectional view of the diaper illustrated in FIG. 9a.

DETAILED DESCRIPTION OF THE INVENTION

Figure 1:
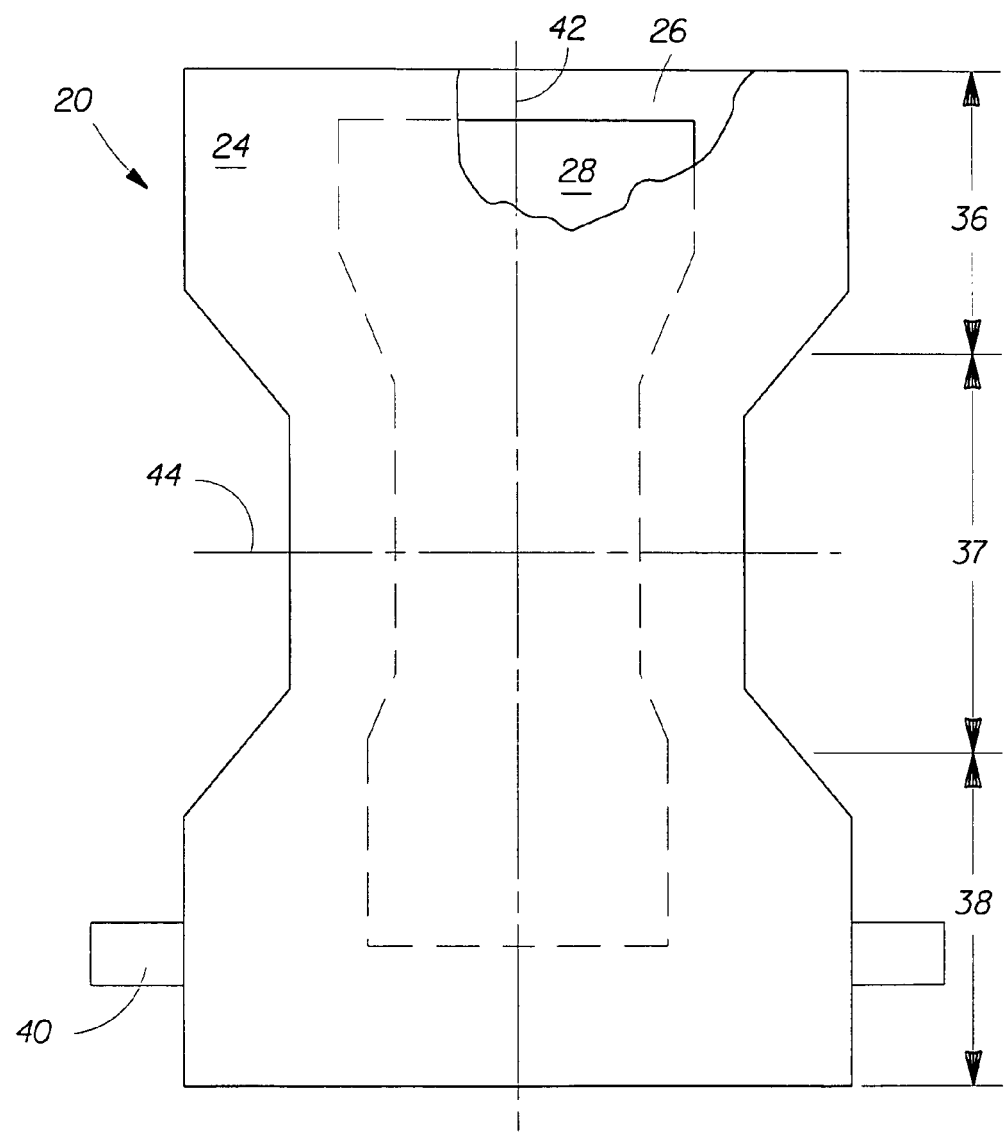
FIG. 1 is a plan view of a disposable diaper.

While this specification concludes with claims particularly pointing out and distinctly claiming that which is regarded as the invention, it is anticipated that the invention can be more readily understood through reading the following detailed description of the invention and study of the included drawings.

The present invention provides a disposable absorbent article having a wetness sensation member that increases a wearer's awareness that urination has occurred by causing the urine discharged from the body of the wearer to wet an effective area of the wetness sensation member, which is preferably held in close contact with the wearer's skin during use. The wetness sensation member is equally applicable to disposable absorbent articles including training pants, pull-on diapers, incontinence briefs, incontinence undergarments, absorbent inserts, diaper holders and liners, feminine hygiene garments, and the like. One exemplary embodiment of an absorbent article of the present invention is a unitary disposable absorbent article, such as the disposable diaper 20, shown in FIG. 1.

Definitions

As used herein, the following terms have the following meanings:

The term "absorbent article" refers to a device that absorbs and contains liquid, and more specifically, refers to a device that is placed against or in proximity to the body of the wearer to absorb and contain the various exudates discharged from the body.

The term "disposable" refers to absorbent articles that generally are not intended to be laundered or otherwise restored or reused as absorbent articles, i.e., they are intended to be discarded after a single use and, preferably, to be recycled, composted or otherwise disposed of in an environmentally compatible manner.

The term "disposed" is used to mean that an element(s) is formed (joined and positioned) in a particular place or position as a unitary structure with other elements or as a separate element joined to another element.

The term "unitary" refers to an absorbent article that is formed of separate parts united together to form a coordinated entity so as to not require separate manipulative parts like a separate holder and liner.

"Diaper" refers to an absorbent article generally worn by infants and incontinent persons about the lower torso.

The term "toilet training" refers to the development of continence, which is the ability to voluntarily retain one's urine and feces. Individuals who are incontinent are unable to voluntarily retain their bodily discharges and, instead, urinate and defecate reflexively. For example, newborn babies are incontinent. Coincident with the development of continence, children typically develop the ability to voluntarily urinate and defecate, and cease reflexive elimination. This development of continence and of voluntary elimination, in place of reflexive elimination, may be accelerated and/or guided by caregivers through associative and conditioning techniques of training the child. For the purpose of the present invention, the term "toilet training" is used to denote training both for continence, itself, and for the voluntary elimination that is associated with continence. It is also noted that the term "toilet training" is synonymous with the term "potty training".

The term "longitudinal" refers to a direction running parallel to the maximum linear dimension of the article and includes directions within ±45° of the longitudinal direction.

The term "lateral" or "transverse" refers to a direction running at a 90 degree angle to the longitudinal direction and includes directions within ±45° of the lateral direction.

The term "x-y plane" refers to the generally planar structure of a sheet material defined by its length and width and lies between the sheet material's two major surfaces regardless of whether or not the sheet material is flat or curved.

The term "z-direction" refers to the direction through the thickness of a sheet material and generally orthogonal to the x-y plane.

The terms "permeable" and "impermeable" refer to the penetrability of materials in the context of the intended usage of disposable absorbent articles. Specifically, the term "permeable" refers to a layer or a layered structure having pores, openings, and/or interconnected void spaces that permit liquid water to pass through its thickness in the absence of a forcing pressure. Conversely, the term "impermeable" refers to a layer or a layered structure through the thickness of which liquid water cannot pass in the absence of a forcing pressure. As is well known in the art, a common method for measuring the permeability of the materials typically used in absorbent articles is a hydrostatic pressure test, also called a hydrostatic head test or simply a "hydrohead" test. Suitable well known compendial methods for hydrohead testing are approved by INDA (formerly the International Nonwovens and Disposables Association, now The Association of the Nonwoven Fabrics Industry) and EDANA (European Disposables And Nonwovens Association).

The terms "retard" and "flow control layer" refer to the fact that different layers in a layered structure may be permeable, yet differ in the respective flow rates at which they permit liquid water, and likewise bodily wastes that are aqueous in nature, to pass through their respective thicknesses. For example, a layer containing capillary channels and through whose thickness liquid water wicks in the absence of any forcing pressure is considered to be permeable. However, the flow rate at which liquid water can pass through the thickness of such a layer may be lower than the flow rate at which liquid water can pass through the thickness of a layer containing holes that are too large to act as capillary channels. Similarly, two layers both containing capillary channels and through whose thicknesses liquid water wicks in the absence of any forcing pressure are both considered to be permeable. However, the capillary channels in one of the layers may differ in size from those in the other layer or may be more numerous than those in the other layer, such that the wicking flow rate of liquid water through the one layer may be greater than that through the other layer. Thus, in a layered structure, one layer serving as a flow control layer may retard the passage of liquid water through the thickness of the layered structure, relative to the greater flow rate at which another of the layers would permit the passage of the liquid water through its thickness in the absence of the flow control layer. The flow control layer may be impermeable, in which case it may retard the passage of liquid water to such an extent that it effectively prevents the passage of liquid water, i.e., the prevention of the passage of liquid water is included within the meaning of the term "retard".

The term "visible" refers to the quality of being capable of being seen by the naked eye under conditions of normal room lighting or in natural light during the daytime. Becoming "more visible" or "less visible" means changing in visibility to a noticeable extent when viewed under a generally constant or equal lighting condition.

The term "visible highlighting" refers to the visible differentiation of an object such that it noticeably stands out from its surroundings, e.g., by differing in coloration, hue, or tint, by differing in lightness, darkness, or contrast, by differing due to the presence or absence of graphical or solid color forms, or by any other variation serving to create noticeable visible differentiation.

The term "coloring" refers to the effect produced by applying or combining colors in and/or on an object or a portion of an object.

The term "coloration" refers to the arrangement or degree of coloring especially when used to visibly differentiate an object or a portion of an object in order to visibly highlight it.

The term "solid coloring" refers to the unbroken, i.e., uninterrupted, coloring of an area as contrasted with the discrete line-like form of some graphics.

The term "graphic" refers to a product of graphic art or a graphic representation in a pictorial form.

The term "associative correlation" refers to establishing a mutual or reciprocal relation between the visible highlighting and that with which it is being associatively correlated so that an association, i.e. a mental connection or bond, is formed between the two. This term is used in the context of associatively correlating the respective visible forms of the visible highlighting and an externally visible marking in or on the absorbent article as well as in the context of associatively correlating the visible highlighting with the concept of urinary toilet training, For example, associatively correlated graphics may serve in concert to draw attention to an opportunity for urinary toilet training when an absorbent article is viewed prior to its being worn, to provide an externally visible reminder of the presence of the wetness sensation member in the interior of the absorbent article while it is being worn, etc. Similarly, visible highlighting that provides a visual reference to a topic related to urinary toilet training, such as dryness, wetness, or protection from wetness, may serve to associatively correlate the visible highlighting to the concept of urinary toilet training and thereby facilitate an opportunity for urinary toilet training.

The terms "interactively interrelated", "interactively unrelated", "related in subject matter", "unrelated in subject matter", and "related by a common story line" are intended to have the same meanings as in U.S. Pat. No. 6,297,424 issued to Olson et al. on 2 Oct. 2001, U.S. Pat. No. 6,635,797 issued to Olson, et al. on 21 Oct. 2003, and U.S. Pat. No. 6,307,119 issued to Cammarota et al. on 23 Oct. 2001.

FIG. 1 is a plan view of the exemplary diaper 20 in its flat out, uncontracted state, i.e., without elastic induced contraction, with portions of the structure being cut away to more clearly show the underlying structure of the diaper 20 and with the portion of the diaper 20 which contacts the wearer facing the viewer. The diaper 20 includes a longitudinal axis 42 and a transverse axis 44. One end portion 36 of the diaper 20 is configured as a first waist region of the diaper 20. The opposite end portion 38 is configured as a second waist region of the diaper 20. An intermediate portion 37 of the diaper 20 is configured as a crotch region, which extends longitudinally between the first and second waist regions 36 and 38. The waist regions 36 and 38 generally comprise those portions of the diaper 20 which, when worn, encircle the waist of the wearer. The waist regions 36 and 38 may include elastic elements such that they gather about the waist of the wearer to provide improved fit and containment. The crotch region 37 is that portion of the diaper 20 which, when the diaper 20 is worn, is generally positioned between the legs of the wearer.

The diaper 20 preferably comprises a permeable topsheet 24, an impermeable backsheet 26, and an absorbent core 28 encased between the topsheet 24 and the backsheet 26. The topsheet 24 may be fully or partially elasticated or may be foreshortened so as to provide a void space between the topsheet 24 and the core 28. Exemplary structures including elasticized or foreshortened topsheets are described in more detail in U.S. Pat. No. 4,892,536 issued to DesMarais et al. on Jan. 9, 1990, U.S. Pat. No. 4,990,147 issued to Freeland on Feb. 5, 1991, U.S. Pat. No. 5,037,416 issued to Allen et al. on Aug. 6, 1991, and U.S. Pat. No. 5,269,775 issued to Freeland et al. on Dec. 14, 1993.

The diaper 20 may include a fastening system 40 or may be sealed at the sides to form a pull-on diaper and/or training pants. The diaper 20 may also include such other features known in the art, including outer leg cuffs, barrier leg cuffs, front and rear ear panels, waist cap features, elastics, and the like to provide desired fit, containment, and aesthetic characteristics. Such additional features are well known in the art and are described in U.S. Pat. Nos. 3,860,003 and 5,151,092, among others.

Figure 2:
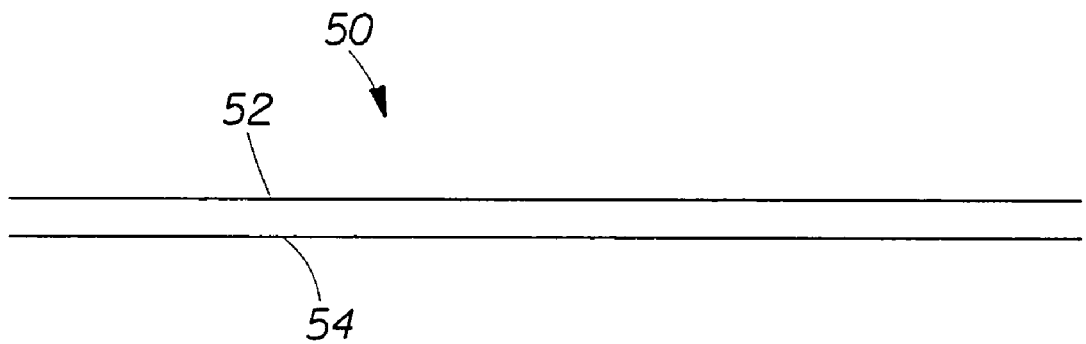
FIG. 2 is a cross sectional view of a wetness sensation member according to the present invention.

An exemplary wetness sensation member according to the present invention is shown in FIG. 2. The wetness sensation member 50 comprises a permeable layer 52 and a flow control layer 54 disposed opposite the permeable layer 52. The flow control layer is preferably impermeable to liquid water but permeable to vapor so that it is breathable. The wetness sensation member 50 according to the present invention preferably comprises a permeable body-facing layer (upper layer) and a flow control layer (lower layer) opposite the body facing layer.

During insults of urine, the permeable layer 52 allows urine to penetrate in the z-direction and also provides a medium for the flow of urine in the x-y plane via wicking. The flow control layer retards the passage of the urine through the wetness sensation member in the z-direction, thereby expanding the wetted area of the wetness sensation member, which preferably is held in contact with the wearer's skin. The combination of limited penetration in the z-direction and wicking in the x-y plane causes the urine to spread out and effectively wet a large area before being absorbed into the absorbent core, thereby maximizing the wetness signal experienced by the wearer.

Exemplary permeable layers suitable for use in the wetness sensation members of the present invention include nonwovens, foams, woven materials, etc. The permeable layer is preferably hydrophilic. Exemplary flow control layers suitable for use in the wetness sensation members of the present invention include polyolefinic films, microporous or breathable films, other films, and hydrophobic nonwovens. Suitable hydrophobic nonwovens include SM (spunbond meltblown), SMS (spunbond meltblown spunbond), and SMMS (spunbond meltblown meltblown spunbond) composites.

In the absorbent articles of the present invention, visible highlighting is provided to indicate the presence of the wetness sensation member or members in the article and thereby facilitate an opportunity for the urinary toilet training of the wearer of the article. Although a wetness sensation member lacking this visible highlighting is fully functional in terms of providing a noticeable wetness signal to the wearer, the caregiver might overlook or forget the possibility of capitalizing on each opportunity for urinary toilet training if the body-facing portion of the absorbent article presents a generally uniform appearance. For example, many absorbent articles present a generally uniform white appearance on their body-facing surfaces. Even if the caregiver were to attempt to enlist the cooperation of the wearer in urinary toilet training, such a uniform appearance provides no visual cues to draw the interest of the wearer to the wetness sensation member and no specific portion to which the caregiver can point while explaining the upcoming opportunity to the wearer. On the other hand, by providing visible highlighting to indicate the presence of the wetness sensation member, an opportunity for urinary toilet training can be facilitated. If the caregiver would have otherwise overlooked the presence of the wetness sensation member or simply forgotten about the possibility of capitalizing on a particular application of the absorbent article onto the body of the wearer to explain the urinary toilet training opportunity to the wearer, the visible highlighting can serve to capture the caregiver's attention and thereby remind her or him of the opportunity.

Furthermore, once the caregiver decides to mention urinary toilet training to the wearer, the visible highlighting can serve to draw the wearer's interest or can be pointed out by the caregiver and incorporated into an explanation of the upcoming opportunity. For example, if the visible highlighting includes a graphic such as an object recognizable by the wearer, the caregiver can ask the wearer to try not to get the recognizable object wet while wearing the absorbent article and, instead, to be sure to remember to ask to go to the toilet in time to avoid getting it wet. Similarly, the caregiver can ask the wearer to tell her or him whenever the wearer thinks that the recognizable object might have gotten wet. Thus, the visible highlighting can provide a topic for conversation between the caregiver and the wearer on the subject of urinary toilet training and can likewise provide a nameable object for reference by the wearer, greatly simplifying the mental task required of the wearer who desires to communicate his or her need to go to the toilet or to communicate his or her improving recognition of the wetness signal provided by the wetness sensation member.

Even a simple solid coloring form of visible highlighting can serve to facilitate an opportunity for urinary toilet training, especially when used with wearers possessing some recognition of colors or colored forms. In addition, visible highlighting in the form of a color or colors may facilitate the teaching of recognition of colors and differences between colors, and the associated learning may enhance the urinary toilet training process in turn. For instance, the occurrence of a color similar to the color of the visible highlighting in a toy or another object may be used to remind the wearer of the same color inside the absorbent article and its significance. As another example, the color itself can serve as the recognizable "object" that is incorporated into the explanation of the opportunity for urinary toilet training, as described above.

Because the wetness sensation member is located in what may be generally termed the laterally central region of the absorbent article, visibly highlighting it may provide additional benefits related to the learning achieved by the wearer. For example, a visibly highlighted wetness sensation member may provide a line of reference for the visual separation of the two leg openings, including their differentiation into right and left leg openings for the respective feet to be inserted into the corresponding leg openings. Such a visual cue may be particularly helpful when the interior of the article is otherwise entirely one color, such as all white. In such a case an oral instruction to, for example, place one foot on either side of the visible highlighting visual reference would likely be more effective than a vague instruction to place both feet through the holes, i.e., the leg openings. Similarly, a longitudinally oriented visible highlighting may serve as a visual reference for the front to back direction, both for orienting the article prior to applying it, if done by the caregiver, or prior to donning it, if done by the wearer. This longitudinally oriented visual reference may also aid in the teaching of such skills as wiping one's self clean after using the toilet by using a longitudinal motion. The concept of something being central or "in the middle" may be taught and learned by visual reference to the visible highlighting and this concept may then be applied to related subjects, such as the anatomical location of the source of urine and the corresponding proper position in which to sit on the toilet. For example, a link can be made for the wearer that he or she urinates "in the middle" on the visibly highlighted area of the absorbent article and so it is important to sit "in the middle" on the potty. Thus, in the above and similar ways, the wearer can be made more aware of his or her own body, which may tend to enhance and facilitate the urinary toilet training experience.

In addition, the visible highlighting can serve to enhance the self-esteem of the wearer through a reminder that he or she is mature enough to be engaged in urinary toilet training. This effect can be compounded when the wearer succeeds in recognizing the need to go to the toilet and then sees the dry condition of the visibly highlighted wetness sensation member inside the article after pulling it down in preparation for using the toilet.

The visible highlighting may be provided by means of printing onto a surface of the wetness sensation member or one of its layers. For example, solid coloring or a graphic may be printed onto a surface of the flow control layer underlying the permeable layer. As another example, an adhesive or a gel may be printed onto a surface of either of the two layers. Such an adhesive or gel may be colored differently from the surrounding area. Alternatively, the adhesive or gel may be uncolored or may have the same color as the surrounding area, but may still provide visible highlighting by forming a distinctive raised area or pattern and/or by surrounding a distinctive recessed area or pattern.

The visible highlighting may also be provided by forming one or more layers of the wetness sensation member of a colored material, for example, a fibrous layer containing colored fibers, a monolithic layer containing a dispersed or imbedded colorant, a layer of an unbleached material that is colored in its virgin state, and so on.

In some embodiments, the visible highlighting may be provided by impressing or embossing the wetness sensation member or one of it layers. As one example, the permeable body-facing layer of the wetness sensation member may be embossed in a pattern that serves to draw the attention of the caregiver or the wearer. As another example, the permeable layer and the flow control layer may be bonded together in discrete locations or along discrete lines and the bonds may form a pattern similarly serving to draw the attention of the caregiver or the wearer.

The impressed, embossed, or bonded portions of the wetness sensation member may provide a tactile sensation in addition to visibly highlighting the presence and location of the wetness sensation member. For instance, a raised area or a recessed area or the combination of raised and recessed areas adjacent to each other may be felt by the hand and, in some embodiments, may be felt by the wearer while wearing the article. Similarly, the raised area or pattern formed by a printed adhesive or gel, as mentioned above, may provide such a tactile sensation. Just as with the visible highlighting alone, the combination of visible highlighting and this tactile sensation can serve to draw the wearer's interest or can be pointed out by the caregiver and incorporated into an explanation of the upcoming opportunity for urinary toilet training. For example, if both a visible highlighting and tactilely sensible pattern are provided in the article, the caregiver can have the wearer feel the "bumpy" area and ask the wearer to try not to get the "little bumps" wet while wearing the absorbent article and, instead, to be sure to remember to ask to go to the toilet in time to avoid getting the "little bumps" wet. Similarly, the caregiver can ask the wearer to tell her or him whenever the wearer thinks that the "little bumps" might have gotten wet. Thus, the visible highlighting in combination with the tactilely sensible pattern can provide a topic for conversation between the caregiver and the wearer on the subject of urinary toilet training and can likewise provide a nameable object for reference by the wearer, greatly simplifying the mental task required of the wearer who desires to communicate his or her need to go to the toilet or to communicate his or her improving recognition of the wetness signal provided by the wetness sensation member. In addition, in some embodiments, the tactilely sensible pattern may serve to temporarily contain small amounts of urine in its depressions, recesses, and/or voids between raised portions and thereby enhance the wearer's awareness that urination has occurred by adding to the wet feeling provided by the layered structure of the wetness sensation member.

In addition, the visible highlighting may be provided by incorporating distinctive fibers or filaments in one or both layers of the wetness sensation member or by distinctively orienting fibers or filaments in one of these layers. For example, a fiber or a filament of a distinctive color may be incorporated into the flow control material to visibly highlight its presence and its location in the article. Similarly, a distinctively thicker fiber or filament may be embedded in one of the two layers and thereby form a distinctive raised area or pattern.

If the portions of the structure of the absorbent article surrounding the wetness sensation member are of one color, the visible highlighting can be provided by the use of another color, by the use of contrast, by the use of a different pattern in the same or a similar color, or by any other method that visibly differentiates the wetness sensation member from the surrounding structural elements. For instance, if the surrounding structural elements are generally white in color, the visible highlighting may include the use of a color other than white. On the other hand, if the surrounding structural elements are not white, the visible highlighting may include the use of a shade of white to visibly differentiate the wetness sensation member. For example, in an embodiment in which a layer of the absorbent core underlying the wetness sensation member is not white but some darker color, a wetness sensation member may be visibly highlighted by including a shade of white in its coloration to visibly differentiate it.

In some embodiments, the visible highlighting may include more than one color, more than one difference in contrast, more than one pattern, more than one graphic, more than one area of solid coloring, and so on, such that all portions of this description referring to the singular of a form of visible highlighting are meant to include the plural, and vice versa.

The visible highlighting may include open or closed geometric figures, such as a partial or a complete circle, square, triangle, diamond, oval, etc. The visible highlighting may include a two dimensional representation of a three dimensional object, such as a cube or another rectangular volume, a sphere, a cylinder, a "doughnut" shape, a bent or curved or twisted version of one of these objects, etc. Similarly, the visible highlighting may include a representation of a commonly named or nameable shape or object, such as a star, a heart, a liquid droplet, a teardrop, a spiral, a wave form, an arrow, a flower, a bubble, dots, etc. In some embodiments, the visible highlighting may include a representation of a recognizable object used in play, such as a ball, a bat, a racket, a badminton shuttlecock (also known as a "birdie"), toy blocks, etc. Also, in some embodiments, the visible highlighting may include a representation of a character that may be known to the wearer, such as a teddy bear, a character appearing on a television show for children, a character appearing in a game or a storybook for children, etc. In embodiments in which the visible highlighting includes a variety of figures, objects, and/or characters, the various elements of the visible highlighting may be interactively interrelated, related by subject matter, and/or related by a common story line. Conversely, the various elements may be interactively unrelated, unrelated by subject matter, and/or not related by a common story line.

When solid coloring is used, it may partially or completely fill the area bounded by a graphic outline, appear as shading inside or outside such a graphic outline, itself form a "filled-in" graphic, or simply uninterruptedly occupy an area, e.g., occupy the entire width of a layer of the wetness sensation member over all or a portion of the corresponding length.

In some embodiments, the visible highlighting may become more or less visible when the wetness sensation member is wetted. In addition, the visible highlighting may change color when the wetness sensation member is wetted. Any of these effects may be created by the use of inks or dyes or other agents that undergo chemical reactions or are dispersed or concentrated when wetted by urine. In general, any of the wetness indicating compositions commonly used in externally visible wetness indicators, such as so-called "appearing" or "disappearing" wetness indicators that may become more or less visible when wetted and in wetness indicators that may change color when wetted, may be used for these versions of visible highlighting. Such wetness indicating compositions are well known in the art and need not be described in detail here.

It is important to note that the visible highlighting of the present invention serves to visibly differentiate the wetness sensation member, which is located between the wearer's body and the absorbent core. Thus, rather than being structurally disposed in such a way as to provide a wetness indication that is visible from the outside of the absorbent article, any wetness indicating compositions used for the visible highlighting of the wetness sensation member must be visible from the body-facing surface of the absorbent article. This different disposition enables the caregiver to apply different techniques to the task of urinary toilet training when using an absorbent article of the present invention, as compared to using an absorbent article having only a wetness indicator visible from the outside of the article. For example, while the change in an exterior wetness indicator is visible for all to see, any change in the visible highlighting of an interior wetness sensation member remains "private" until either the caregiver or the wearer peers into the absorbent article or it is removed. Therefore, whether or not any wetting of the absorbent article has occurred can, itself, become the focus of a playful activity resembling a game, with the "secret" being revealed only when the caregiver and the wearer agree to conclude the game. If the wearer has successfully maintained control of his or her urination and has not wet into the absorbent article, this fact can become a source of pride at the accomplishment and can be "proven" by the wearer by pointing out to the caregiver that the visible highlighting has not changed in appearance. On the other hand, if the wearer notices a sensation of wetness or merely desires to check the condition of the "private" indication, he or she can simply look inside the absorbent article. If the appearance of the visible highlighting has changed, the wearer can then choose to bring this to the attention of the caregiver in the context of asking to go to the bathroom. In addition, because the visible highlighting serves as a "private" indication, the wearer might be able to detect a change in its appearance before the appearance of any externally visible wetness indicator changes and thereby be the first person to mention the subject of going to the toilet, i.e., the wearer may be enabled to visually detect the wetting of the absorbent article prior to the time at which the caregiver could detect the same condition by visual reference to the externally visible wetness indicator. Furthermore, the provision of both visual and tactile sensations to the wearer may serve to reinforce the tactile sensation of wetness and thereby enhance the training effect of the wetness sensation member. An absorbent article in which the wetting is indicated by both a wetness sensation and a visible change in the appearance of the visible highlighting may thus facilitate faster learning on the part of the wearer.

Although the appearance of the visible highlighting remains "private" until either the caregiver or the wearer peers into the absorbent article or it is removed, the visible highlighting may be associatively correlated in visible form with marking that is located elsewhere in or on the absorbent article and is visible from the outside of the absorbent article. This externally visible marking may be permanent or may change in appearance while the absorbent article is being worn. For example, the externally visible marking may be an externally visible wetness indicator. By giving the visible highlighting of the wetness sensation member a visible form that is similar to the visible form of an externally visible marking, an opportunity for urinary toilet training may be enhanced. For instance, the caregiver can point out the similarity between the externally visible marking and the "private" visible highlighting of the wetness sensation member and ask the wearer to remember the hidden visible highlighting every time he or she notices the externally visible marking. The similarity may also be referenced at another time, for example when initiating the "game" of checking the "private" indication, i.e., the visible highlighting, by drawing the wearer's attention to the unchanged appearance of an externally visible wetness indicator while asking what the wearer thinks will be seen when the "private" visible highlighting is checked for a sign of whether or not the wearer has wet into the absorbent article.

Even in embodiments in which the appearance of the visible highlighting is not affected by its being wetted, the associative correlation of the respective visible forms of an externally visible marking and the visible highlighting may serve to facilitate an opportunity for urinary toilet training. For example, if both the externally visible marking and the visible highlighting have the visible form of similar graphics, the externally visible marking can serve to draw the wearer's interest or can be pointed out by the caregiver and incorporated into an explanation of the ongoing opportunity for urinary toilet training. If both the externally visible marking and the visible highlighting include a graphic such as an object recognizable by the wearer, the caregiver can remind the wearer to try not to get the recognizable object wet while wearing the absorbent article and, instead, to be sure to remember to ask to go to the toilet in time to avoid getting it wet. Similarly, the caregiver can ask the wearer to tell her or him whenever the wearer thinks that the recognizable object might have gotten wet. Thus, the associatively correlated combination of the externally visible marking and the visible highlighting can provide a topic for conversation between the caregiver and the wearer on the subject of urinary toilet training and can likewise provide a nameable object for reference by the wearer, greatly simplifying the mental task required of the wearer who desires to communicate his or her need to go to the toilet or to communicate his or her improving recognition of the wetness signal provided by the wetness sensation member.

Such associative correlation of the respective visible forms of an externally visible marking and the visible highlighting can be achieved without the respective visible forms being similar, so long as the respective visible forms are mutually related in a recognizable way. The visible forms may be related in subject matter. For example, the externally visible marking may show a character wearing a soccer uniform and the associatively correlated visible highlighting may show a soccer ball. As another example, the visible highlighting may show swim fins and the associatively correlated externally visible marking may show a swim mask. The visible forms may be related by a common story and may also be interactively interrelated. For example, the externally visible marking may show a character holding a butterfly net and the associatively correlated visible highlighting may show butterflies.

Even an associative correlation of a simple solid coloring form of an externally visible marking with a similar solid coloring form of visible highlighting can serve to facilitate an opportunity for urinary toilet training, especially when used with wearers possessing some recognition of colors or colored forms. In addition, an associative correlation of an externally visible marking with visible highlighting in the form of a color or colors may facilitate the teaching of recognition of colors and differences between colors, and the associated learning may enhance the urinary toilet training process in turn. For instance, the occurrence of a color similar to the color of both the externally visible marking and the visible highlighting in a toy or another object may be used to remind the wearer of the same color inside the absorbent article and its significance. As another example, the color itself can serve as the recognizable "object" that is incorporated into the explanation of the opportunity for urinary toilet training, as described above.

Alternatively, the visible highlighting may be associatively uncorrelated with any externally visible marking. The lack of associative correlation may be complete or may be specific, e.g., the respective visible forms of the visible highlighting and the externally visible marking may be unrelated in subject matter, not related by a common story line, and/or interactively unrelated, while still being associatively correlated in another way.

Figure 3A:
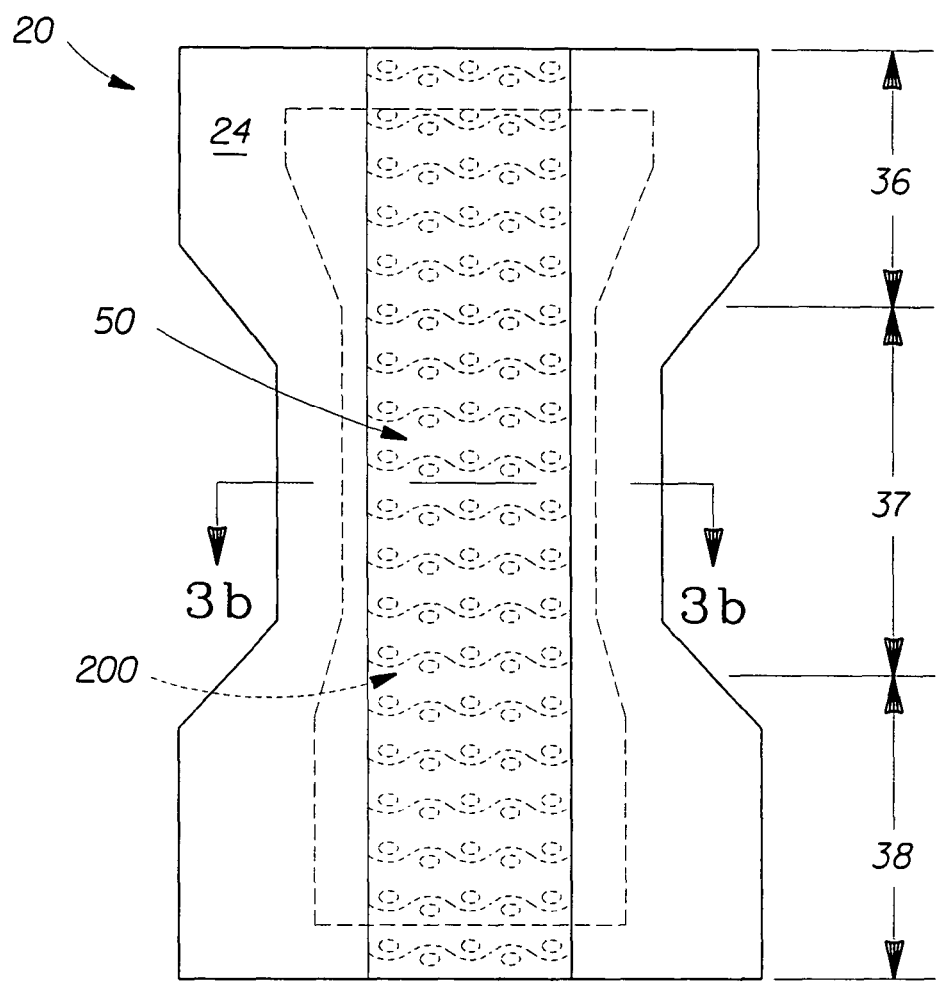
FIG. 3a is a plan view of a diaper having a wetness sensation member disposed on a body-facing surface.

The visible form of the visible highlighting of the wetness sensation member need not be associatively correlated with the concept of urinary toilet training. However, in some embodiments, the visible form of the visible highlighting may be associatively correlated with the concept of urinary toilet training by, for example, providing a visual reference to the liquid-related nature of urinary toilet training, such as wetness, dryness, protection from wetness, the flow of a liquid, water, et cetera, and thus may serve to facilitate an opportunity for urinary toilet training. For example, on the theme of water, the visible highlighting may include a depiction of droplets of water, ducks, a bath toy, beach toys, waves, a watering can, a teapot, swim gear such as flippers, a mask, a snorkel, etc. The visible highlighting 200 in FIG. 3a represents an exemplary visible highlighting in the visible form of water waves and bubbles. Other ways of referencing the watery nature of urinary toilet training in the visible highlighting may include a depiction of marine life forms, such as fish, dolphins, porpoises, whales, or any other aquatic creature that may be recognizable by the wearer.

The visible highlighting may emphasize dryness by depicting the sun, fair weather clouds, a sunny day, etc., while wetness may be referenced by a depiction of a water puddle, a cloud with falling rain, etc. A visual reference to protection from wetness may be provided by a depiction of an umbrella, a raincoat, a rain hat, galoshes, a submarine, or some other object that may be associated by the wearer with the concept of staying dry in a wet environment. The associative correlation of the visible form of the visible highlighting with the concept of urinary toilet training may be even more explicit. For example, a depiction of a potty chair may serve to provide a more literal visual reference for the wearer to the desired behavior. As another example, a depiction of a "big kid" in an appropriate posture in relation to a potty chair or a toilet bowl may similarly provide such a literal visual reference.

In any of these visible forms of visible highlighting that are associatively correlated with the concept of urinary toilet training, a human form and/or a recognizable character may be depicted in the visible highlighting. For example, a child may be shown in conjunction with inanimate objects, a child may be shown sitting on a potty chair, and/or a character from a children's storybook or a children's television program may be shown in similar poses, etc.

The benefits of the wetness sensation member can be shown by comparison of the strikethrough time for a given sample of wetness sensation member and a topsheet material, alone. Strikethrough time is the time required for a given volume of surface-applied liquid to enter a given material into an underlying absorbent core. The testing is performed according to the Topsheet Strikethrough Time Test Procedure that is provided in U.S. Pat. No. 6,627,786 issued on 30 Sep. 2003 in the name of Roe et al. As is described in the Roe et al. '786 patent, testing that was performed on a topsheet material composed of 18 $g/m^2$ spunbond nonwoven and a wetness sensation member composed of an 18 $g/m^2$ spunbond nonwoven laminated to a 20 $g/m^2$ SMMS nonwoven via a 6 $g/m^2$ adhesive revealed the wetness sensation member to have a strikethrough time on the average about 3.4 times the strikethrough time of the topsheet material, alone.

The ability of a wetness sensation member to support the flow of liquid in the x-y plane can be measured by its wicking capability. The wicking capability of the wetness sensation member is measured according to INDA Standard test: IST 10.1 (95) Paragraph 10 Liquid Wicking Rate. The test is the measure of the time in seconds for liquid to wick vertically 1.0 inch (approximately 25.4 mm). As also described in the Roe et al. '786 patent, testing of the same topsheet material and the same wetness sensation member revealed that the wetness sensation member supported vertical wicking of 1.0 inch (approximately 25.4 mm) in an average time of 6.8 seconds, whereas the topsheet material, alone, was incapable of supporting vertical wicking to a height of 1.0-inch (approximately 25.4 mm).

The wetness sensation member according to the present invention may be arranged in an absorbent article in a variety of configurations. In addition, absorbent articles may include a single wetness sensation member or a plurality of wetness sensation members. In any event, the wetness sensation member(s) are preferably a part of, or attached to, an element or web, such as a topsheet, which is reliably held against the skin of the wearer. The wetness sensation member 50 may extend over a portion of the disposable absorbent article spanning less than one half of the length of the article or else extend over a substantial part of the article spanning more than one half the length of the article. In addition, the wetness sensation member(s) are preferably positioned within the absorbent article to enhance the likelihood of being wetted with urine.

Figure 3B:
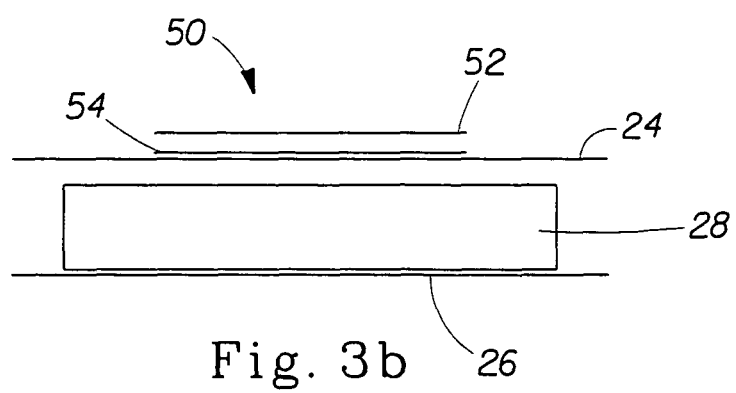
FIG. 3b is a cross sectional view of the diaper shown in FIG. 3a illustrating the layers of the wetness sensation member.

An exemplary embodiment of a wetness sensation member 50 disposed with the topsheet 24 is illustrated in FIG. 3a and FIG. 3b. As shown, the wetness sensation member 50 comprises a separate composite member attached to the topsheet 24. The wetness sensation member 50 comprises a permeable body-facing layer 52, and a flow control layer 54 opposite the body-facing layer. For this embodiment, the wetness sensation member 50 is preferably configured and assembled to enhance the likelihood of making contact with the wearer's skin during use. For instance, the flow control layer 54 of the wetness sensation member 50 may be bonded to the topsheet 24 using adhesives, ultrasonic bonds, radio frequency bonds, or other suitable means while either the topsheet 24 or the wetness sensation member 50 is elastically foreshortened to deflect the member 50 toward the wearer's skin. The visible highlighting 200 is shown in FIG. 3a as a pattern of wavy lines and circles.

Figure 4:
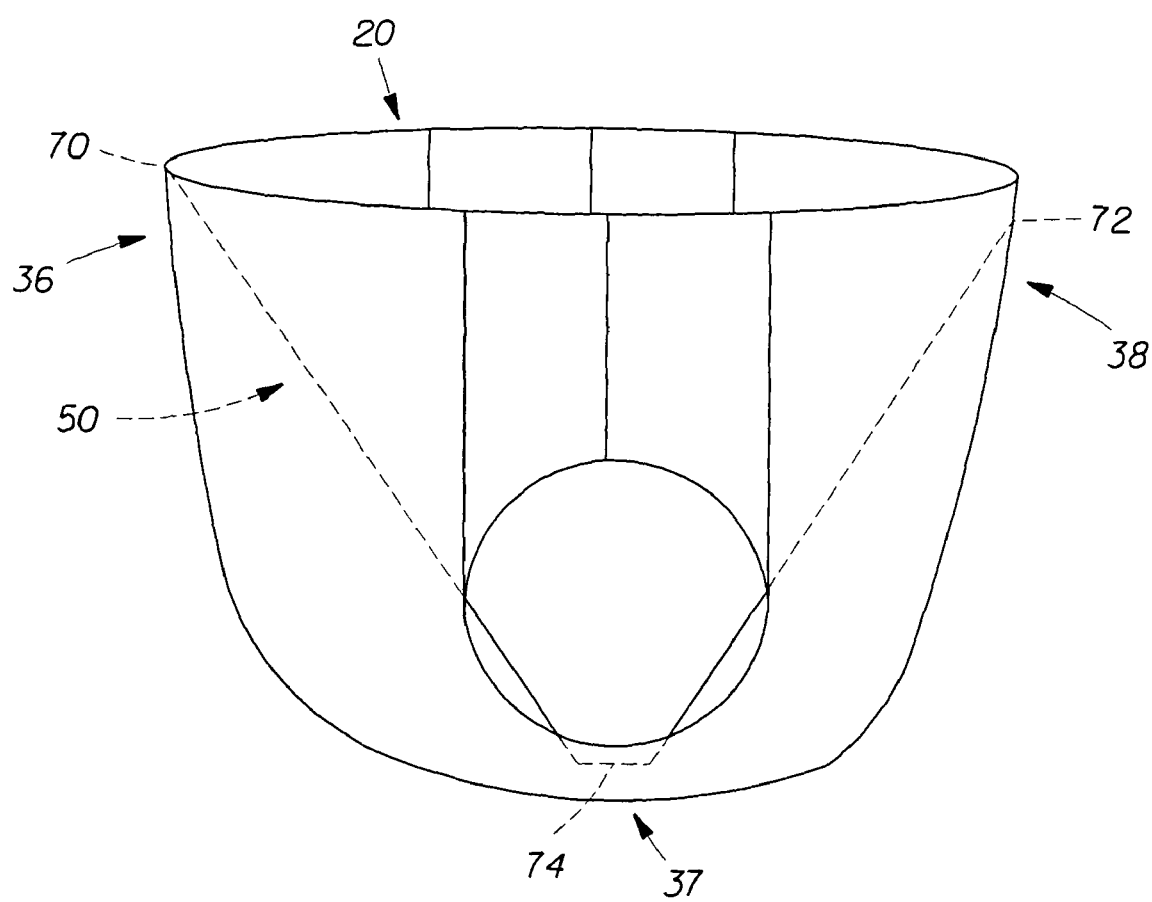
FIG. 4 is an isometric view of a pull-on diaper illustrating the attachment of the wetness sensation member.

In an embodiment illustrated in FIG. 4, a wetness sensation member 50 comprising a separate composite member is disposed on the topsheet 24 of a pull-on type diaper. For this embodiment, the wetness sensation member 50 has elastic properties and includes a first longitudinal end 70 attached to the first waist region 36 and a second longitudinal end 72 attached to the second waist region 38. In addition, a center portion 74 of the member 50 is preferably attached to the crotch region 37 of the diaper 20 in order to stabilize the member and facilitate fitting the article to the wearer, prevent interference with bowel movements and ensure good contact with the wearer's skin.

Figure 5A:
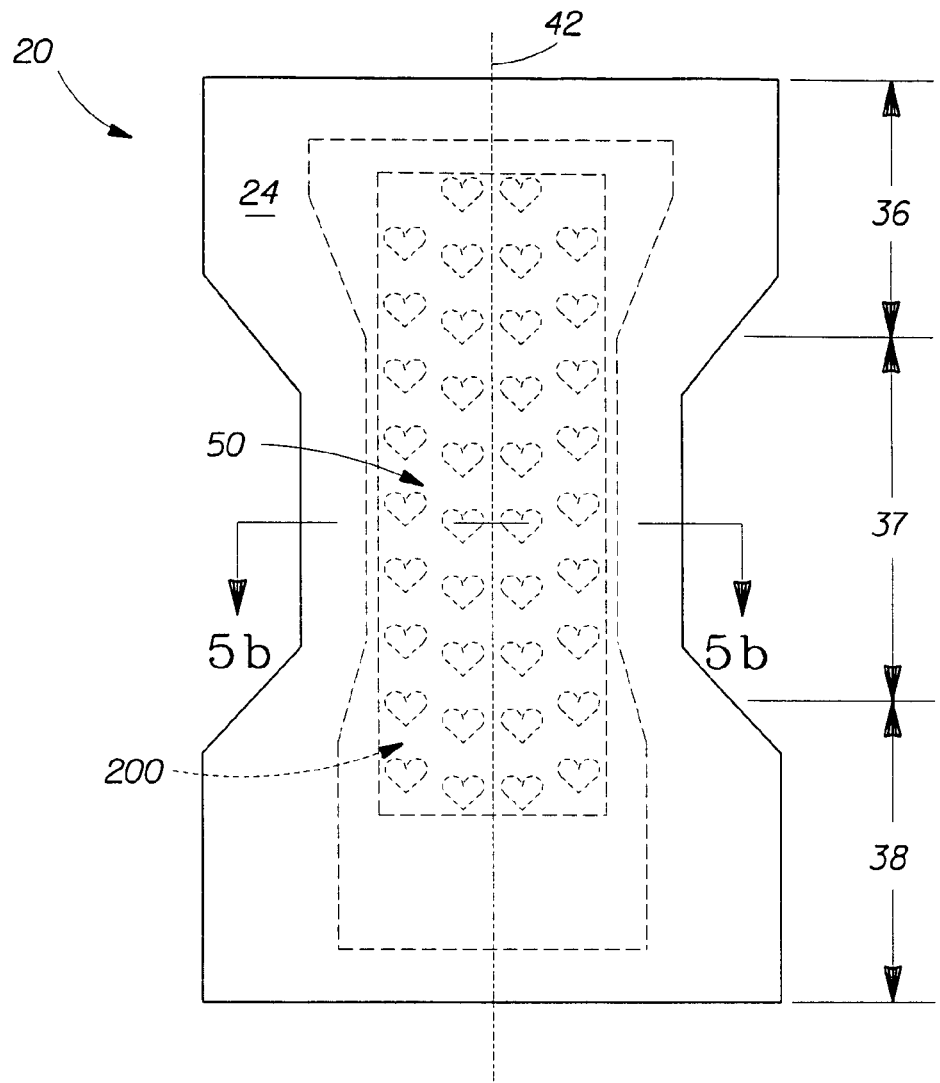
FIG. 5a is a plan view of a diaper having a wetness sensation member integrated with the topsheet.
Figure 5B:
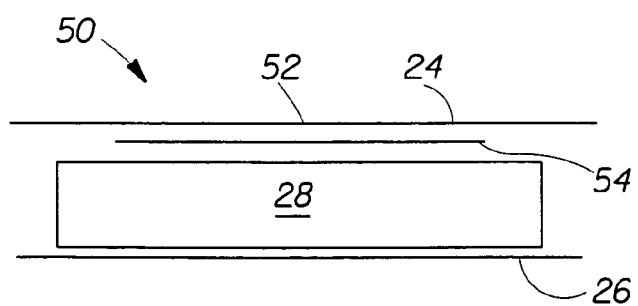

In an alternate embodiment shown in FIG. 5a and FIG. 5b, the flow control layer 54 of the wetness sensation member 50 is attached to the inner surface of the topsheet 24 such that at least a portion of the topsheet 24 forms the permeable layer 52 of the wetness sensation member 50. For this embodiment, the topsheet 24 is preferably elastically foreshortened to deflect the wetness sensation member 50 into contact with the wearer's skin. Alternatively, this embodiment may include a topsheet that is shorter in length than the backsheet, having the longitudinal ends of the topsheet contiguous with the longitudinal ends of the backsheet so that as the diaper is fitted around the wearer, the topsheet is forced into contact with the wearer's skin. The visible highlighting 200 is shown in FIG. 5a as a pattern of heart shapes.

Regardless of the specific construction, the position and/or structure of the wetness sensation member 50 should enable the member to be wetted with urine and thereafter held in contact with the wearer's skin. In some preferred embodiments, the wetness sensation member is disposed in at least a portion of the crotch region 37 of the diaper 20, centered about the longitudinal centerline 42. Furthermore, in these exemplary embodiments, the wetness sensation member 50 is preferably coordinated with the wearer's urethra in order to cover the area in which urine first comes into contact with the disposable absorbent article.

Figure 6A:
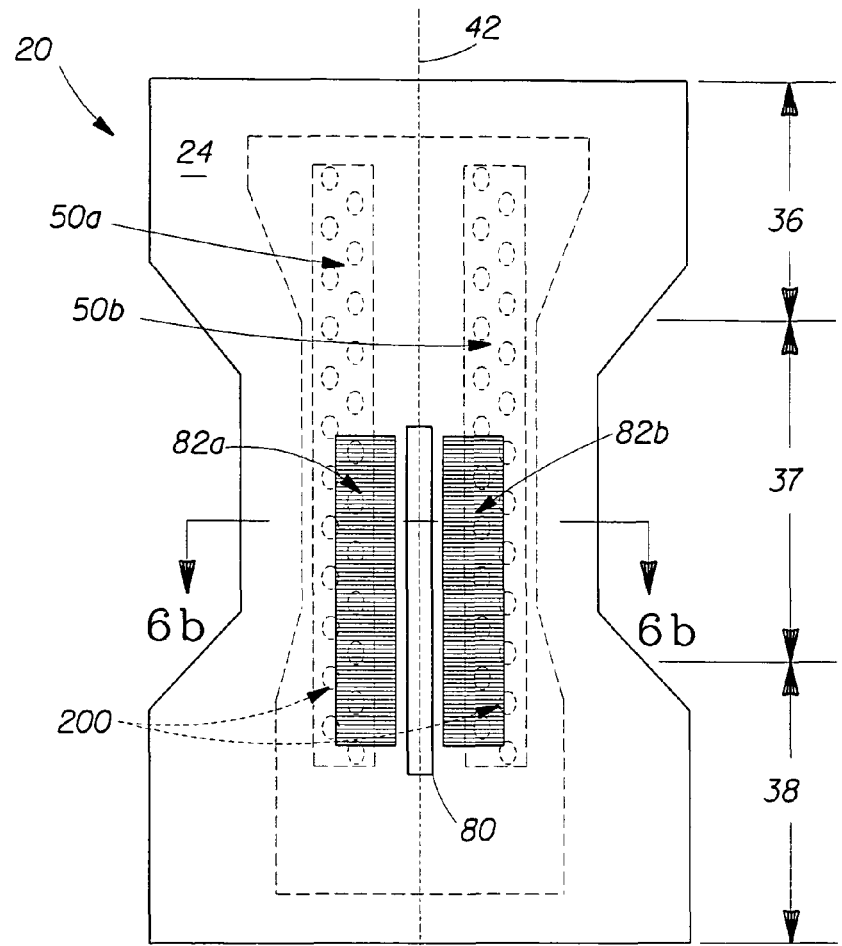
FIG. 6a is a plan view of a diaper having two wetness sensation members integrated with the topsheet and disposed parallel to and spaced apart from the longitudinal axis with an elongated slit opening interposed therebetween.
Figure 6B:
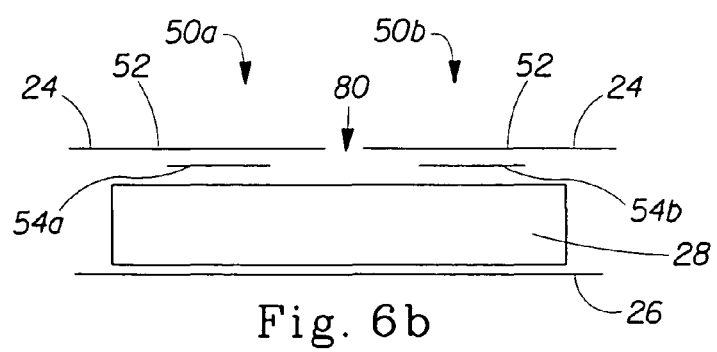

Absorbent articles according to the present invention may include a plurality of wetness sensation members disposed on the body-facing surface of the article. An example of an embodiment providing a plurality of wetness sensation members is shown in FIG. 6a and FIG. 6b. Two flow control layers 54a and 54b, are attached to the bottom surface of the topsheet 24 forming two wetness sensation members 50a and 50b. For this embodiment, the flow control layers 54a and 54b are disposed between the topsheet and the absorbent core 28 so that the topsheet forms the permeable layers 52 of the wetness sensation members. The two flow control layers 54*a* and 54*b* are disposed parallel to and spaced apart from the longitudinal centerline 42 of the diaper 20. The spacing is determined to allow enough liquid to pass through to the core so as to prevent flooding that can result in leakage of the absorbent article during urination, while at the same time enable enough liquid to flow and wick toward the flow control layers forming the wetness sensation members. The spacing between the flow control layers can be about 10 mm but can range from about 5 mm to about 15 mm and from about 8 mm and to about 12 mm. For this embodiment, the flow control layers 54*a* and 54*b* are attached to the lower side of the topsheet 24 using adhesives, ultrasonic bonds, radio frequency bonds, or other suitable means. The attachment can comprise bonds covering the entire interface between the flow control layers and the topsheet, spot bonds or bonds along the longitudinal and transverse edges of the flow control layers. Although the embodiment shown in FIG. 6*a* and FIG. 6*b* has only two wetness sensation members, other absorbent article embodiments having three or more wetness sensation members are contemplated. The visible highlighting 200 is shown in FIG. 6*a* as a pattern of oblong ovaloid shapes.

As shown in FIG. 6*a* and FIG. 6*b*, the spacing of the flow control layers provides room for an elongated slit opening 80 in the topsheet 24. The elongated slit opening 80 is adapted to receive feces from the wearer and isolate the same from the wearer's skin. As shown, the slit opening 80 is preferably interposed between the wetness sensation members 50*a* and 50*b* along the longitudinal centerline 42 of the diaper 20. The elasticized regions 82*a* and 82*b* located adjacent to the slit opening 80 maintain alignment of the slit opening 80 with the wearer's anus during use. The elasticized regions 82*a* and 82*b* may also deflect the wetness sensation members 50*a* and 50*b* toward the wearer's skin to maintain contact therewith during use. Exemplary elasticized topsheets including elongated slit openings are disclosed in U.S. Pat. No. 6,482,191 issued 19 Nov. 2002 in the name of Roe et al.

Alternatively, the flow control layers 54*a* and 54*b* of the wetness sensation members 50*a* and 50*b* may be elastically foreshortened to provide benefits similar to those provided by the elasticized regions 82*a* and 82*b* disposed in the topsheet 24.

Figure 7A:
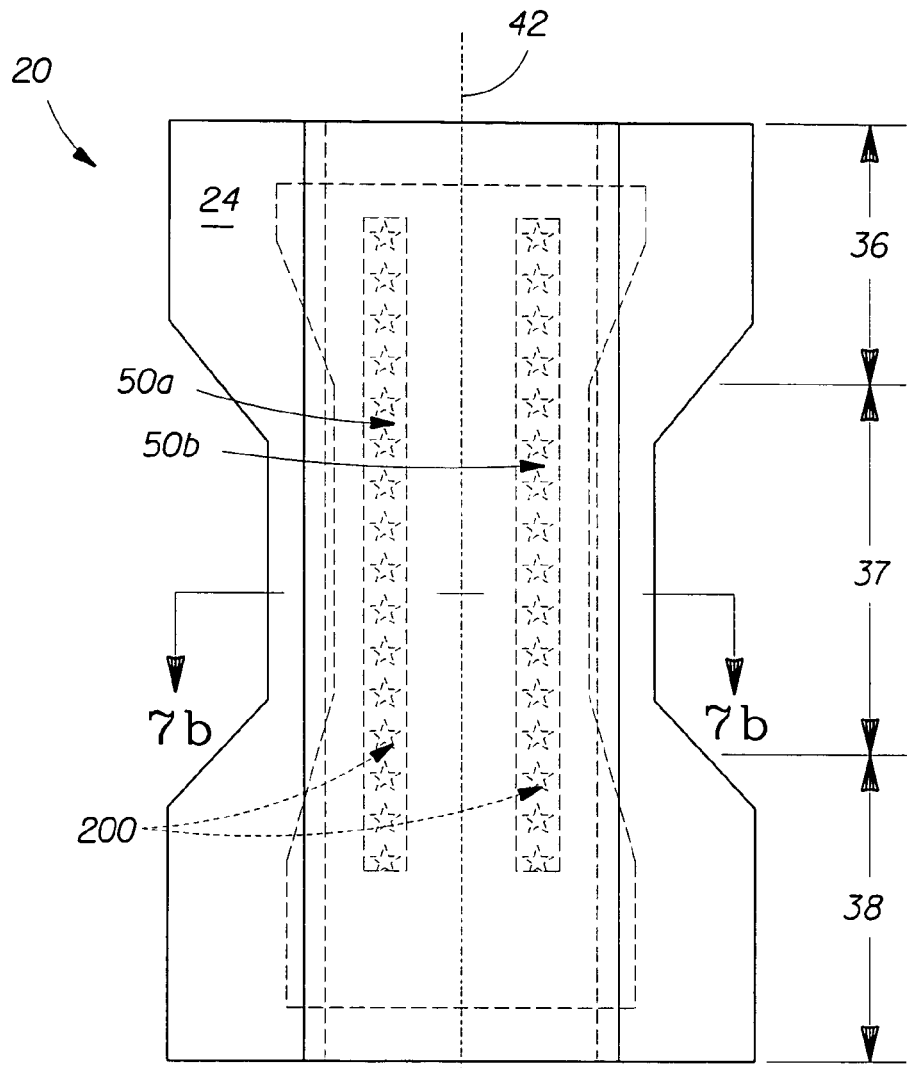
FIG. 7a is a plan view of a diaper having a Z-folded topsheet with two wetness sensation members integrated with the topsheet and disposed in the Z-folds in the topsheet.
Figure 7B:
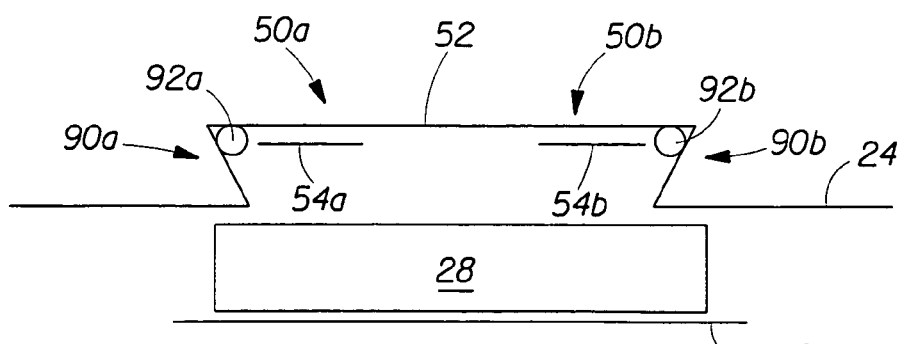

In another alternate embodiment shown in FIG. 7*a* and FIG. 7*b*, the topsheet 24 forms the permeable layer 52 similar to the previous embodiment, however, the flow control layers 54*a*, 54*b* are disposed in two parallel Z-folds 90 formed in the topsheet 24 along the longitudinal length of the diaper 20. The Z-folded topsheet may be attached to the underlying layers along the longitudinal edges of the topsheet 24 allowing the portion between the Z-folds of the topsheet 24 to float freely. Elastic elements 92 are disposed along the flow control layers 54*a* and 54*b* in order to deflect the center portion of the Z-folded topsheet outward away from the absorbent core 28. The elastic elements 92 may be disposed along the outer edges of the flow control layers 54*a* and 54*b* as shown in FIG. 7*b*, or alternatively, may be disposed in face-to-face relationship with the flow control layers 54*a* and 54*b*. The combination of the Z-folded topsheet 24 and the elastic elements 92 maintains the wetness sensation members in contact with the wearer's skin in the event that the diaper sags or fits loosely around the wearer. The visible highlighting 200 is shown in FIG. 7*a* as a pattern of star shapes.

In order to prevent the portion of the topsheet between the Z-folds from being forced into the gluteal groove and from interfering with the barrier leg cuffs, the spacing between the Z-folds can be about 65 mm and can range from about 50 mm to about 90 mm. Further, in order to control the deflection of the portion of the topsheet between the Z-folds, transverse bonds may be formed between the Z-folds in the first waist region, the second waist region and the crotch region using adhesives, ultrasonic bonds, radio frequency bonds, or other suitable means in order to control deflection. These transverse bonds attach the Z-folded section to the body-facing surface of the topsheet and the section between the Z-folds to the underlying core.

In addition to integrating the wetness sensation member with the topsheet, the wetness sensation member of the present invention may also be integrated with other components of the diaper such as the barrier leg cuffs. The barrier leg cuffs may be made from either permeable or impermeable material. In either case, the barrier leg cuff material may form one of the layers of the wetness sensation member. In such exemplary embodiments, the structure of the barrier leg cuffs preferably holds the wetness sensation members in contact with the skin of the wearer to provide the sensation of wetness against the wearer's legs and/or crotch crease.

Figure 8A:
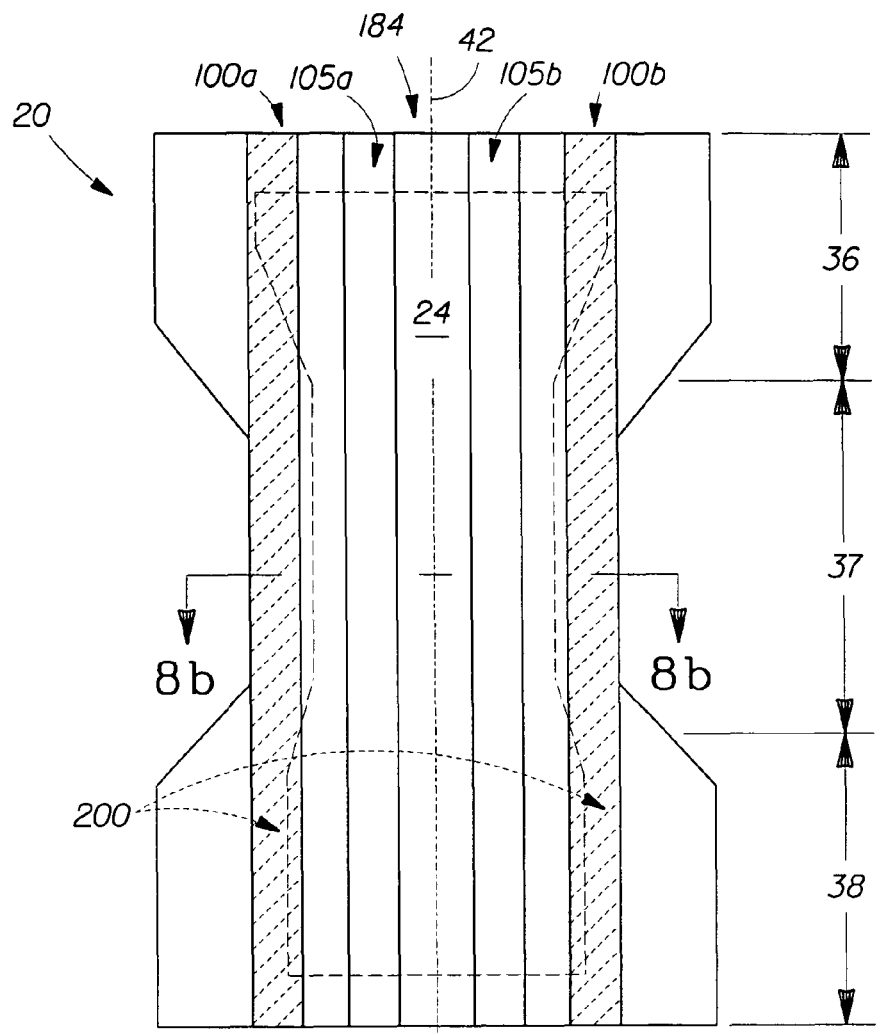
FIG. 8a is a plan view of a diaper with barrier leg cuffs including wetness sensation members integrated with the barrier leg cuffs.
Figure 8B:
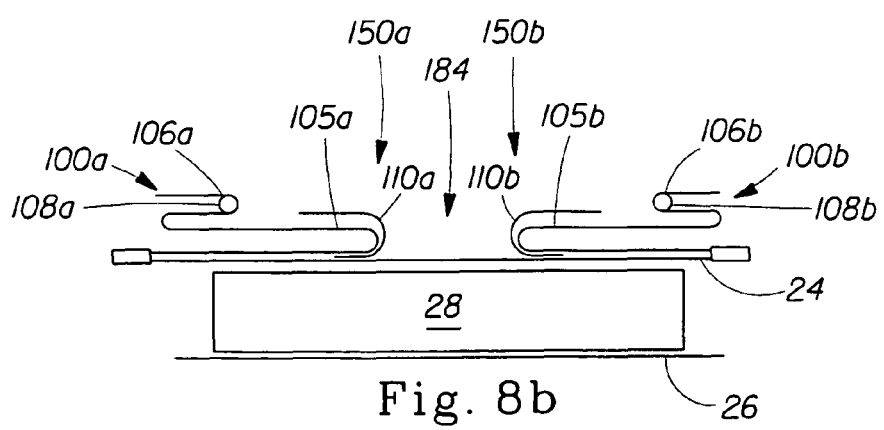

An example of wetness sensation members integrated with the barrier leg cuffs is shown in FIG. 8*a* and FIG. 8*b*. The diaper 20 for this embodiment includes barrier leg cuffs 100*a* and 100*b* made from impermeable material. The barrier leg cuffs 100*a* and 100*b* extend along the longitudinal edges of the diaper 20 in a parallel arrangement disposed on the body-facing surface of the topsheet 24 leaving an exposed center portion 184 of the topsheet 24 therebetween. For the embodiment shown in FIG. 8*a* and FIG. 8*b*, the wetness sensation members 150*a* and 150*b* are integrated with the barrier leg cuffs 100*a* and 100*b* such that the barrier leg cuff material provides the flow control layer of the wetness sensation members. The permeable layers 110*a* and 110*b* can extend the length of each of the barrier leg cuffs and preferably extend at least the length of the crotch region 37 and the front waist region 36. The permeable layers 110*a* and 110*b* are preferably disposed on portions of the cuffs closest to the longitudinal axis 42 of the diaper 20 to increase the likelihood of becoming wetted during urination. As shown in FIG. 8*a* and FIG. 8*b*, the barrier leg cuffs 100*a* and 100*b* include Z-folded configurations with inner folds 105*a* and 105*b* disposed near the longitudinal axis 42 of the diaper 20 leaving a center portion 184 of the topsheet 24 exposed. The Z-folded leg cuffs 100*a* and 100*b* also include outer folds 106*a* and 106*b* having elastic elements 108 disposed therein. During use, the elastic elements 108 deflect the leg cuffs away from the topsheet 24, toward the skin of the wearer. The visible highlighting 200 is shown in FIG. 8*a* as a pattern of angled lines.

Figure 9A:
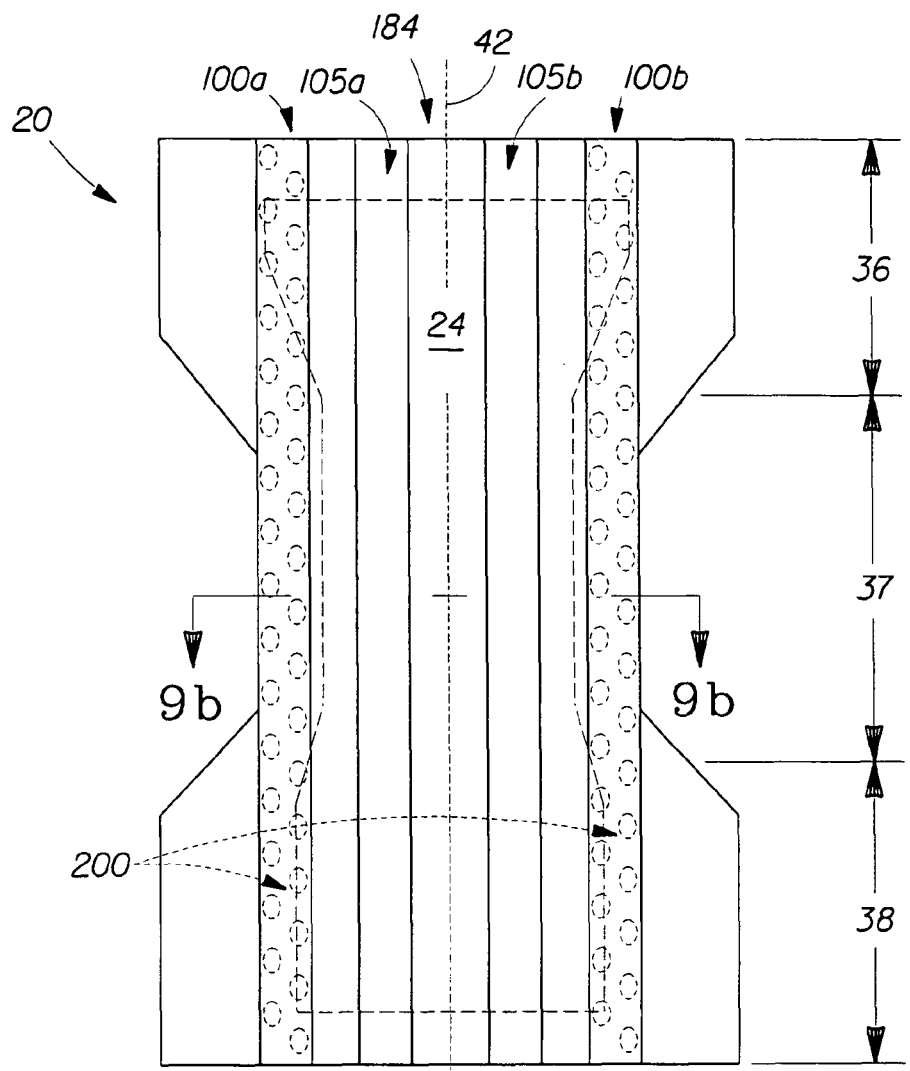
FIG. 9a is a plan view of a diaper with an alternative form of barrier leg cuffs including wetness sensation members integrated with the barrier leg cuffs.
Figure 9B:
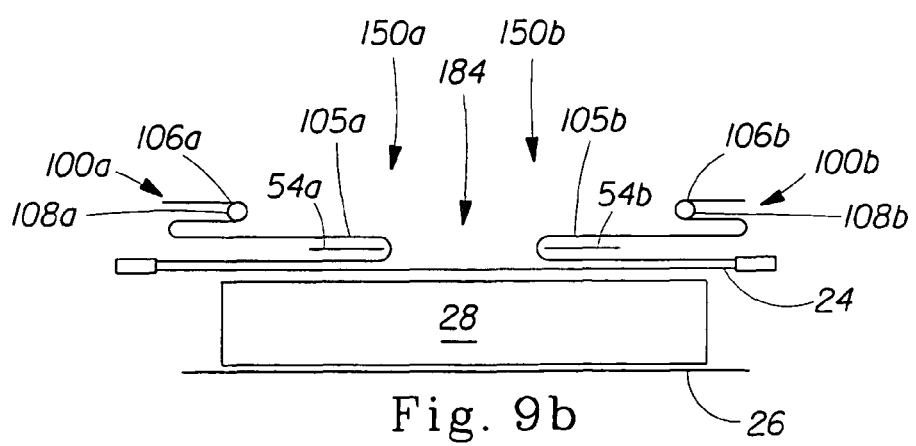

Another example of wetness sensation members integrated with barrier leg cuffs is shown in FIG. 9*a* and FIG. 9*b*. In this embodiment, the barrier leg cuffs 100*a* and 100*b* are made of a permeable material and are otherwise arranged similarly to the embodiment shown in FIG. 8*a* and FIG. 8*b*. However, because the barrier leg cuff material forms the permeable body-facing layer of each of the wetness sensations members 150*a* and 150*b* in this embodiment, flow control layers 54*a* and 54*b* are located between the absorbent core and each respective permeable layer formed by the barrier leg cuff material. The visible highlighting 200 is shown in FIG. 9*a* as a pattern of oval shapes.

The embodiments of wetness sensation members disclosed hereunder perform most effectively when held in contact with the skin of the wearer. In order to ensure that contact is made with the wearer's skin during use, the body-facing portion of the wetness sensation members may include a body-adhering composition, such as a topical adhesive, which acts to hold the wetness sensation member in place during use. The body-adhering composition may be applied to at least a portion of the body-facing surface of the wetness sensation member. However, the body-adhering composition may also be integral with the material making up the body-facing layer of the wetness sensation member. Further, the body-adhering composition may be disposed on any portion of the wetness sensation member contacting the skin of the wearer in any pattern or configuration including, but not limited to lines, stripes, dots, and the like.

Such a body-adhering composition may include any of one or more substances capable of releasably adhering to the skin of the wearer. Some exemplary hydrogel and/or hydrocolloid adhesives are disclosed in U.S. Pat. Nos. 4,231,369, 4,593,053, 4,699,146, 4,738,257, and 5,726,250. Suitable exemplary medical adhesives are described in U.S. Pat. Nos. 4,078,568, 4,140,115, 4,192,785, 4,393,080, 4,505,976, 4,551,490, and 4,768,503, and suitable polyacrylate and polymethacrylate hydrogel adhesives are disclosed in U.S. Pat. Nos. 5,614,586 and 5,674,275. Yet another exemplary adhesive comprising polyvinyl pyrrolidone and a multi-functional amine-containing polymer is disclosed in WO 94/13235A1. It is preferred that the body-adhering composition permit vapors to pass, i.e., be breathable, be compatible with the skin and otherwise skin-friendly. Further, it is preferred that the body-adhering composition be at least partially hydrophobic such that it preferably contains 60% and more preferably 80% hydrophobic components by weight. However, hydrophilic compositions are contemplated in certain embodiments of the present invention.

The disclosures of all patents, patent applications, and any patents which issue thereon, as well as any corresponding published foreign patent applications, and all publications listed and/or referenced in this description, are hereby incorporated herein by reference. It is expressly not admitted, however, that any of the documents or any combination of the documents incorporated herein by reference teaches or discloses the present invention.

While particular embodiments and/or individual features of the present invention have been illustrated and described, it would be obvious to those skilled in the art that various other changes and modifications can be made without departing from the spirit and scope of the invention. Further, it should be apparent that all combinations of such embodiments and features are possible and can result in preferred executions of the invention. Therefore, the appended claims are intended to cover all such changes and modifications that are within the scope of this invention.

What is claimed is:

1. A disposable absorbent article for wearing about a lower torso of a wearer and having a longitudinal axis, two laterally opposed article side edges extending between a laterally extending first waist end edge in a first waist region and a laterally extending second waist end edge in a second waist region, and a crotch region interposed therebetween, the disposable absorbent article comprising:
   a backsheet;
   a topsheet joined to the backsheet and having a body-facing surface;
   an absorbent core disposed intermediate the backsheet and the topsheet;
   at least one wetness sensation member disposed upon the topsheet in a face-to-face arrangement with the permeable body-facing layer and having two laterally opposed side edges, at least a portion of each of the two wetness sensation member side edges being disposed laterally inwardly of the article side edges; and
   a visible highlighting indicating a presence of the wetness sensation member in the disposable absorbent article and being visible at least when viewing the body-facing surface of the topsheet to facilitate an opportunity for urinary toilet training of the wearer wherein said visible highlighting comprises an ink-printed pattern made up of a plurality of repeating figures and wherein said ink-printed pattern is visible prior to wetting of the wetness sensation member, and wherein the appearance of the visible highlighting is substantially unchanged upon wetting of the wetness sensation member,
   wherein urine deposited by the wearer onto the wetness sensation member can penetrate through the permeable body-facing layer in a z direction away from the wearer to the absorbent core and the wetness sensation member retards the passage of the urine in the z direction and supports the movement of the urine in an x-y plane such that the wearer's awareness of urination is enhanced.

2. The disposable absorbent article of claim 1 comprising a plurality of the wetness sensation members disposed parallel to and spaced apart from the longitudinal axis and spaced apart from one another, each of the wetness sensation members being disposed upon the topsheet.

3. The disposable absorbent article of claim 2 wherein the plurality of wetness sensation members are separated from one another by a spacing ranging from about 5 mm to about 15 mm.

4. The disposable absorbent article of claim 2 wherein the topsheet comprises two Z-folds parallel to the longitudinal axis and each of the wetness sensation members is disposed within a respective one of the two Z-folds.

5. The disposable absorbent article of claim 4 wherein the two Z-folds are separated by a spacing ranging from about 50 mm to about 90 mm.

6. The disposable absorbent article of claim 4 wherein the two Z-folds further comprise two elastic members disposed along the two flow control layers.

\* \* \* \* \*

UNITED STATES PATENT AND TRADEMARK OFFICE
CERTIFICATE OF CORRECTION

| | | |
|---|---|---|
| PATENT NO. | : 7,767,876 B2 | Page 1 of 1 |
| APPLICATION NO. | : 10/697225 | |
| DATED | : August 3, 2010 | |
| INVENTOR(S) | : Mary Elizabeth Davis et al. | |

It is certified that error appears in the above-identified patent and that said Letters Patent is hereby corrected as shown below:

Column 15
Line 39, delete "S0b" and insert --50b--.

Signed and Sealed this
Twenty-second Day of March, 2011

David J. Kappos
*Director of the United States Patent and Trademark Office*